United States Patent [19]

Zilberman et al.

[11] Patent Number: 5,356,544
[45] Date of Patent: Oct. 18, 1994

[54] METHOD FOR THE PREPARATION OF METAL SOAP AQUEOUS DISPERSIONS

[75] Inventors: Ekhiel Zilberman, Acre; Felix Lerner, Karmiel, both of Israel

[73] Assignee: Electrochemical Industries (Frutarom) Ltd., Israel

[21] Appl. No.: 72,222

[22] Filed: Jun. 3, 1993

[30] Foreign Application Priority Data

Sep. 6, 1992 [IL] Israel .................................... 103068

[51] Int. Cl.$^5$ ........................................ C10M 129/40
[52] U.S. Cl. ..................................... 252/17; 252/49.3; 252/39; 252/40
[58] Field of Search ..................... 252/39, 40, 49.3, 17

[56] References Cited

U.S. PATENT DOCUMENTS

| | | | |
|---|---|---|---|
| 2,137,494 | 11/1938 | Jolly et al. | 252/39 |
| 2,339,715 | 1/1944 | McOmie et al. | 252/49.3 |
| 2,413,220 | 12/1946 | Elder et al. | 252/39 |
| 3,313,729 | 4/1967 | Glasson et al. | 252/49.3 |
| 4,029,682 | 6/1977 | Foulks, Jr. | 252/39 |
| 4,997,479 | 3/1991 | Hou et al. | 252/49.3 |

Primary Examiner—Jacqueline V. Howard
Attorney, Agent, or Firm—Morgan & Finnegan

[57] ABSTRACT

An improved method for preparing aqueous dispersions of metal soaps in the presence of an ionic surfactant formed in-situ is described. The method comprises two main steps: (a) partially neutralizing a saturated or unsaturated fatty acid containing between 8 to 28 carbon atoms with an alkali metal oxide or hydroxide including ammonia and (b) mixing the resulted dispersion with an aqueous dispersion of a metal oxide or hydroxide, said metal being selected from calcium, magnesium, calcined calcium carbonate, calcined dolomite, strontium, barium and any mixture thereof. The preferred alkali metal used in step (a) is selected from lithium, sodium, potassium and any mixture thereof. The fatty acid used in step (a) is selected from stearic acid, palmitic acid, myristic acid, oleic acid, linoleic acid and any mixture thereof. The concentration of the aqueous dispersion of metal soaps is generally in the range of between 0.2% to 50% by weight. The aqueous dispersions of metal soaps were found to be useful as additives for improving the flowability of polymer materials.

15 Claims, No Drawings

METHOD FOR THE PREPARATION OF METAL SOAP AQUEOUS DISPERSIONS

The present invention relates to a novel method for the preparation of aqueous dispersions of metal soaps. More particularly, the invention relates to a novel method for the preparation of metal soaps obtained in the presence of an ionic surfactant formed in-situ.

BACKGROUND OF THE INVENTION

The use of metal soap aqueous dispersions as additives useful for many purposes, such as: improving the flowability of polymers and especially of polyvinyl chloride, as lubricant for paper coating, in SBR as waterproofing agent, as thickeners, etc. This appears from a large number of patents published in the last twenty years on this subject. Some of these references are describing the improvement obtained in the flowability of polyvinyl chloride powder, thus preventing a decrease in its bulk density due to a static build-up on suspension polymers of vinyl chloride.

Metal salts of carboxylic acids containing between 8 to 28 carbon atoms are known as soaps. The characteristic feature of metal soap aqueous dispersions is the presence of a water insoluble carboxylate salt.

According to Japanese Patent Number 59' 51,236 (mentioned in C.A.101, 40223), metal soaps aqueous dispersions were obtained by homogenizing powdered calcium stearate, oleate or palmitate with water, in the presence of surfactants selected from ethoxylated lauryl alcohol and sodium dodecyl sulfate.

According to another Japanese Patent Application 76 34904 (mentioned in C.A. 85,23038), slurries of metal soaps having high concentrations of active constituents are prepared by the reaction of alkali salts of fatty acid with water-soluble metal salts at a temperature of between 65° to 105° C. in the presence of a surfactant. An example as given in the abstract, is calcium stearate slurry, prepared from sodium stearate, a solution of calcium chloride and polyoxyethylene nonylphenyl ether.

In the German (East) Patent Number 106,629 (mentioned in C.A. 82,74823), metal soap dispersions are prepared from stearin, water, an ethylene oxide-alkylphenol condensate, acetic acid and calcium hydroxide, or zinc oxide at a temperature of between 85° to 90° C. As an advantage of the method it is mentioned that the final product contained less than 0.17% of free fatty acid. However, the main disadvantage of the methods described in the above two patents, is the fact that water soluble salts, sodium chloride—in the first one—and calcium acetate—in the second one—which resulted as by-products in the respective reactions involved, remain in the final dispersions. This is a significant disadvantage,since these impurities are detracting the electrical properties of the resin.

An interesting method for obtaining a homogenized aqueous dispersion of calcium stearate, zinc stearate and calcium oleate, is described in the Japanese Patent Application Number 82'77642 (mentioned in C.A. 97, 91751). The main feature of the method for obtaining the dispersion is that the reagents—free acids and calcium hydroxide,—in the presence of an anionic surfactant containing a lyophilic alkyl phenol, or higher alcohol residue, are thoroughly mixed by a mechanical device under high pressure.

A similar method is also described in a very recent Japanese Kokai Application 02'191,539 (mentioned in C.A. 114, 8456). As realized, the use of pressure which requires special equipment, mentioned to impart a good storage stability, is a significant inconveniency of these methods.

One of the main disadvantage of all the above methods, is the fact that a non-ionic surfactant is incorporated and it remains in the final product causing soiling of the dispersion of the metal soap. Furthermore, it is well-known that the emulsifying agents are generally reducing the thermal and storage stability of resins and particularly of polyvinyl chloride.

The above brief review of the prior art, illustrates the problems which exist to-day for preparing metal soap aqueous dispersions, without detracting by their incorporation in the polymers processing, the properties of the final products obtained.

It is an object of the present invention to provide a novel method for the manufacture of metal soap aqueous dispersions. It is another object of the present invention, to provide a novel method for the manufacture of metal soap aqueous dispersions, without adding a non-ionic surfactant. It is a further object of the present invention, to provide a novel method for the manufacture of metal soap aqueous dispersions, wherein a ionic surfactant is formed in-situ and does not remain in the final product. It is yet another object of the present invention, to provide a method for obtaining metal soap aqueous dispersion, which are not containing any foreign impurity from the starting reagents.

BRIEF DESCRIPTION OF THE INVENTION

The invention relates to a method for preparing metal soap aqueous dispersions in the presence of an ionic surfactant which comprises the steps of: (a) partially neutralizing a fatty acid containing between 8 and 28 carbon atoms with an alkali metal oxide or hydroxide including ammonia, thus obtaining an aqueous dispersion of said fatty acid, and (b) mixing said dispersion with an aqueous dispersion or solution of a metal oxide, or hydroxide of Group II. According to a most preferred embodiment, the amount of fatty acid at the end of the two steps, is substantially the stoichiometrical required in order to neutralize the metal hydroxide or metal oxide of Group II. The extent of neutralization in step (a) may be selected in a broad range of between 0.5% to 99% and preferably between 2% to 30%. One of the main advantages of the method, is the fact that an ionic surfactant is utilized being formed in-situ. The aqueous dispersions obtained will be acid-free and their consistencies as well as their particle sizes may be controlled and thus selected according to the specific use of the aqueous dispersions.

DETAILED DESCRIPTION OF THE INVENTION

The method according to the present invention, enables to obtain aqueous dispersions of metal soaps of any concentration in the range of between 0.1% to 80% and particularly between 0.2% to 50%, which are generally used in the art.

The temperature at which the reactions involved are carried out, may be selected from a very broad range. Thus aqueous dispersions, based on liquid fatty acids, may be prepared even at room temperature. Higher temperatures than the melting point of the fatty acid may be employed, but the most preferred temperature is slightly higher than the melting point of the respective fatty acid used.

The fatty acids generally used for this reaction, may be selected from known saturated and unsaturated acids having between 8 and 28 carbon atoms. Typical examples of such acids are: stearic, palmitic, myristic, oleic, linoleic or any mixture thereof.

The neutralization of the fatty acid in the first step, is a known reaction which goes smoothly according to the amount of alkali including ammonia, introduced in the reaction, being completed in a very short time in the order of seconds. In this manner, an aqueous dispersion of the fatty acid, stabilized by its corresponding alkali salt as an ionic surfactant is formed.

In the second step, the reaction time will be in the order of few minutes, going smoothly due to the presence of a surfactant obtained in-situ in the first step. The short reaction time, in this case, may also be explained by the fact that the alkaline salts of fatty acids, play also the role of a phase transfer agent.

In the second step, the dispersion obtained in the first stage is mixed with a metal oxide or hydroxide of Group II, preferably in the form of an aqueous dispersion, when a better contact between the reagents occurs. Typical examples of the metals useful in this reaction are calcium, magnesium, barium, strontium, or any mixture thereof. One may also conceive to use in this reaction any unexpensive material which contains any of these constituents such as calcined or partially calcined carbonates of these metals and especially dolomite due to its abundancy, in view of the fact that a certain amount of carbonate present therein, does not interfer the method.

The order of addition of the reagents is not critical. The most preferred way, is to add the dispersion of the metal oxide or hydroxide of Group II to the aqueous dispersion containing the fatty acid. In this manner a complete conversion of the fatty acid to the respective salt of the metal of Group II is achieved.

The method according to the present invention, does not require the incorporation of the relatively expensive anionic surfactants into the final product, as mentioned in the prior art. Moreover, the ionic surfactant which is formed in-situ, will disappear in the final product, due to the displacement of the alkaline metal cation, by the cation of the metal from Group II, producing the respective metal soap. In case, that for some specific purpose, it is requested to leave in the final product some of the ionic surfactant, this can be easily achieved according to the amounts of reactants used in the system.

The invention will be hereinafter described by a number of Examples, which should be considered as illustrative being presented only for a better understanding of the invention without limiting its scope, which will be covered by the appended Claims. A person skilled in the art, after reading the present specification, will be in a position to select the proper conditions and amounts of reagents, in order to obtain the desired product.

In the Examples, the concentrations are given in weight percentage, unless otherwise stated.

EXAMPLE 1

An amount of 1.2 ml (0.6 mmol) of a solution of sodium lo hydroxide (0.5N) was added to a mixture consisting of 90 ml water and 5.70 g (20 mmol) stearic acid (m.p. 54° C.). The dispersion obtained was heated to 60° C. under a continuous stirring.

In the second step, an amount of 0.74 g (10 mmol) of calcium hydroxide was added to 200 ml of water and heated to 60° C. under stirring. The slurry obtained is then gradually added to the first dispersion during 10 minutes under a vigorous stirring, the temperature being kept at 60° to 62° C. for about thirty minutes.

The resulted dispersion contained 6.07 g (2.04%) of calcium stearate, which corresponds to 100% yield and 0.023 g (0.57 mmol) of sodium hydroxide.

After cooling, the particles of calcium stearate were found in the upper part of the vessel, while water was found at the bottom.

The calcium stearate particles were measured by a laser Fritsch particle sizer, the average diameter being 72 μm in a narrow particle size distribution. After a treatment by ultrasound, the average diameter was 53.5 μm.

EXAMPLE 2

An amount of 10 ml (2.9 mmol) of a solution of 0.5% ammonia was added to a mixture of 110 ml water and 5.70 g (20 mmol) of stearic acid. The dispersion obtained was heated to 64° C. under a continuous stirring.

In the second stage, an amount of 0.74 g (10 mmol) of calcium hydroxide was added to 200 ml water and heated to 6° C. under stirring. The heated dispersion was gradually added during eight minutes to the heated dispersion of stearic acid while the stirring continued for an additional period of 30 minutes.

The final dispersion contained 6.07 g (1.86%) of calcium stearate, which was acid-free, having a pH of 8.0.

The dispersion was uniform throughout the whole volume and did not show any separation after one day.

The average diameter of the particles of calcium stearate as measured by a laser Fritsch instrument, was 55.8 μm. After a treatment by ultrasound, the average diameter was 4.9 μm.

EXAMPLE 3

An amount of 6 ml (6 mmol) of a solution of 1N sodium hydroxide was added to a mixture of 200 ml of water and 28.5 g (100 mmol) of stearic acid. The dispersion obtained was heated to 65° C. under a continuous stirring.

In the second step, an amount of 3.7 g (50 mmol) of calcium hydroxide was added to 150 ml of water and heated to 67° C. under stirring. The heated dispersion was gradually added to the first heated dispersion of stearic acid while a vigorous stirring continued for about 15 minutes. The final dispersion obtained contained 30.3 g (7.8%) of calcium stearate. After cooling, part of the metal soap precipitated.

The average diameter of the particles of calcium stearate as measured by a laser Fritsch instrument, was 23.7 μm.

EXAMPLE 4

The experiment as in Example 1 was repeated; in the first step the stearic acid was added to 20 ml of water, containing 0.032 g (0.8 mmol) of sodium hydroxide.

In the second stage, 0.74 g (10 mmol) of calcium hydroxide were added to 20 ml of water. The two initial dispersions were heated to a temperature between 65° to 70° C.

After cooling, the resulted aqueous product contained 13.1% of calcium stearate in the form of a viscous uniform dispersion, having a viscosity of 800 cps at 25° C.

EXAMPLE 5

The first step as in Example 2 was repeated using the same amounts of reagents at the same reaction conditions.

In the second step, an amount of 1.06 g of a technical grade calcium hydroxide containing 30% of calcium carbonate was added to 200 ml of water. The dispersion was heated to 60° C. under a continuous stirring. The resulted dispersion was added to the dispersion of stearic acid, reaching a pH 8.

The calcium stearate particles were measured as mentioned in Example 2 and found to be of the same size.

EXAMPLE 6

An amount of 6 ml (0.6 mmol) of sodium hydroxide (0.1N) was added to a mixture of 2.57 g (10 mmol) of palmitic acid and 17 ml water and heated at 65° C.

In the second step, an amount of 0.37 g (5 mmol) of calcium hydroxide was added to 15 ml of water and heated to 65° C. under a continuous stirring.

The resulted dispersion was added gradually during 10 minutes to the dispersion of palmitic acid under a vigorous stirring.

After cooling, a stable and uniform dispersion of calcium palmitate (6.7%) resulted in the form of a viscous product.

The average diameter of the particles measured as in Example 2, was 14.2 $\mu$m.

EXAMPLE 7

An amount of 4 ml (0.4 mmol) of sodium hydroxide (0.1N) was added to 2.83 g (10 mmol) of oleic acid.

In the second step, an amount of 0.37 g (5 mmol) of calcium hydroxide was added to 25 ml of water.

The dispersion obtained in the first step containing sodium oleate and oleic acid was gradually added during 15 minutes, under stirring, to the dispersion of calcium hydroxide and a vigorous stirring was continued for about 30 minutes.

The calcium oleate dispersion obtained, in amount of 3.02 g (4.8%) had a viscosity of 9 centipoises at 25° C. On standing, some precipitation of the soap particles was noticed. A day after the dispersion preparation, 60% (of the whole volume) which appear as upper layer was substantially transparent. The average diameter of the particles, measured as above, was 51.9 $\mu$m and after treatment by ultrasound was 45.4 $\mu$m.

EXAMPLE 8

The experiment as in Example 6, was repeated, with the only difference that instead of 4 ml (0.4 mmol) of sodium hydroxide, an amount of 10 ml (1 mmol) was used. All the procedure and reaction conditions were as in Example 7. The viscosity of the dispersion was 12 cps at 25° C.

A day after the dispersion preparation, the upper layer consisted only of about 18% (of the whole volume) being slightly turbid. The average diameter of the particles, measured as above, was 41.4 $\mu$m.

EXAMPLE 9

An amount of 4.5 ml (1.3 mmol) of ammonia (0.5%) was added to a mixture of 70 ml water and 2.85 g (10 mmol) of stearic acid under stirring and heated at 65° C.

In the second step, a dispersion was prepared from 8 g of hydrated barium hydroxide, partially neutralized by a solution of 150 ml water containing carbon dioxide and heated also at the same temperature as in stage 1.

The dispersion of barium hydroxide was slowly added to the dispersion containing the stearic acid and ammonium stearate under a vigorous stirring until the pH reached a value of 8.5.

The resulted aqueous dispersion contained 3.53 g (1.5%) of barium stearate. After cooling, the soap particles appear in the upper portion of the vessel, while the bottom was substantially transparent.

The average diameter of the particles, measured as above, was 8.4 $\mu$m.

We claim:

1. A method for preparing metal soap aqueous dispersions in the presence of an ionic surfactant formed in-situ which comprises the steps of:
    (a) partially neutralizing up to 30% a fatty acid containing between 8 and 28 carbon atoms with an alkali metal oxide or hydroxide including ammonia, obtaining an aqueous dispersion of said fatty acid, and
    (b) mixing said dispersion with an aqueous dispersion of a metal oxide, or hydroxide, the metal being selected from those of Group II.

2. The method according to claim 1, wherein said fatty acid is saturated.

3. The method according to claim 1, wherein said fatty acid is unsaturated.

4. The method according to claim 1, wherein the amount of fatty acid is substantially equal to that stoichiometrically required to neutralize the metal oxide or hydroxide of Group II.

5. The method according to claim 1, wherein the extent of neutralization by the alkali metal oxide, or hydroxide including ammonia used is step (a), is in the range of between 0.5% to 30%.

6. The method according to claim 5, wherein the extent of neutralization is in the range of 2% to 30%.

7. The method according to claim 1, wherein said alkali metal is selected from lithium, sodium, potassium and any mixture thereof.

8. The method according to claim 1, wherein the concentration of the aqueous dispersion of metal soaps is in the range of between 0.2% to 50% by weight.

9. The method according to claim 1, wherein the reaction in step (b) is carried out at a temperature which is above the melting point of the fatty acid utilized.

10. The method according to claim 1, wherein the fatty acid is selected from the group consisting of stearic acid, palmitic acid, myristic acid, oleic acid, linoleic acid and any mixture thereof.

11. The method according to claim 1, wherein the metal, as oxide or hydroxide, used in step (b), is selected from calcium, magnesium, barium, strontium and any mixture thereof.

12. The method according to claim 1, wherein the ionic surfactant is obtained in-situ in step (a) and disappears from the final product due to its reaction in step (b).

13. The method according to claim 1, wherein the particles size of the resulting dispersion may be varied.

14. The method according to claim 1, wherein the metal oxide is a calcium oxide produced from calcined calcium carbonate.

15. The method according to claim 1, wherein the metal oxide is a calcium oxide and magnesium oxide produced from calcined dolomite.

* * * * *